(12) United States Patent
Scetbon (10) Patent No.: US 6,406,423 B1
(45) Date of Patent: Jun. 18, 2002

(54) METHOD FOR SURGICAL TREATMENT OF URINARY INCONTINENCE AND DEVICE FOR CARRYING OUT SAID METHOD

(75) Inventor: Victor Scetbon, Paris (FR)

(73) Assignee: Sofradim Production, Trevoux (FR)

(*) Notice: Subject to any disclaimer, the term of this patent is extended or adjusted under 35 U.S.C. 154(b) by 0 days.

(21) Appl. No.: 09/489,336

(22) Filed: Jan. 21, 2000

(51) Int. Cl.$^7$ .......................... A61F 2/02; A61B 19/00; A61B 17/08

(52) U.S. Cl. .......................... 600/30; 128/898; 606/151

(58) Field of Search .......................... 128/898; 600/30; 606/119, 148, 198, 151; 607/138

(56) References Cited

U.S. PATENT DOCUMENTS

| | | | | |
|---|---|---|---|---|
| 5,112,344 A | * | 5/1992 | Petros | 606/148 |
| 5,836,314 A | * | 11/1998 | Benderev et al. | 128/898 |
| 5,899,909 A | * | 5/1999 | Claren et al. | 606/119 |
| 6,056,688 A | * | 5/2000 | Benderev et al. | 600/30 |
| 6,091,995 A | * | 7/2000 | Ingle et al. | 607/138 |
| 6,099,547 A | * | 8/2000 | Gellman et al. | 606/198 |
| 6,273,852 B1 | | 8/2001 | Lehe et al. | |

OTHER PUBLICATIONS

Petros, P.E.P. and Ulmsten, U.I. An integral theory and its method for the diagnosis and management of female urinary incontinence. *Scand J Urol Nephrol Suppl.* 1993; 153: 1–93. PMID: 8108659.

Ulmsten, U., Henriksson, L., Johnson, P. and Varhos, G. An ambulatory surgical procedure under local anesthesia for treatment of female urinary incontinence. *Int Urogynecol J Pelvic Floor Dysfunct.* 1996; 7(2): 81–86. PMID: 8798092.

Falconer, C., Ekman–Ordeberg, G., Malmstrom, A. and Ulmsten, U. Clinical outcome and changes in connective tissue metabolism after intravaginal slingplasty in stress incontinent women. *Int Urogynecol J Pelvic Floor Dysfunct.* 1996; 7(3): 133–7. PMID: 8913830.

Ulmsten, U. Some reflections and hypotheses on the pathophysiology of female urinary incontinence. *Acta Obstet Gynecol Scand.* 1997; Suppl. 166(76): 3–8.

Petros, P.E.P. and Ulmsten, U.I. Non stress non urge female urinary incontinence—diagnosis and cure: a preliminary report. *Acta Obstet Gynecol Scand.* 1990; 69: Suppl. 153: 69–70.

DeLancey, J.O.L. Structural support of the urethra as it relates to stress urinary incontinence: the hammock hypothesis. *Am J Obstet Gynecol.* 1994; 170: 1713–20.

Bailey, K.V. Clinical investigation into uterine prolapse with stress incontinence: treatment by modified Manchester colporrhaphy part II. *J Obstet Gynaecol Br Emp.* 1956; 63: 663–76.

(List continued on next page.)

Primary Examiner—Eric F. Winakur
Assistant Examiner—Nikita R Veniaminov
(74) Attorney, Agent, or Firm—Oliff & Berridge, PLC (57) ABSTRACT

In a device and method for the percutaneous treatment of urinary stress incontinence in women using a synthetic sub-urethral tape, the device includes a needle, an intermediate traction element, and a sleeved support tape; and the method includes forming an opening in the vaginal wall and forming suprapubic incisions, creating tracks and following one track with a needle and intermediate traction element from a suprapubic incision to the opening in the vagina, following the other track with a needle and optionally an intermediate traction element, verifying the tracks by cystoscopy, passing a sleeved tape through the tracks to form a loop under the urethra, adjusting the loop, removing the sleeve, and leaving the tape implanted.

22 Claims, 6 Drawing Sheets

OTHER PUBLICATIONS

Greenwald, S.W., Thornbury, J.R. and Dunn, L.J. Cystourethrography as a diagnostic aid in stress incontinence. *Obstet Gynecol.* 1967; 29: 324–7.

Faysal, M.H., Constantinou, C.E., Rother, L.F. and Govan, D.E. The impact of bladder neck suspension on the resting and stress urethral pressure profile: a prospective study comparing controls with incontinent patients preoperatively and postoperatively. *J Urol Neurol Urodyn.* 1981; 125: 55–60.

Wang, A.C. and Lo, T.S. Tension–free vaginal tape. A minimally invasive solution to stress urinary incontinence in women. *The Journal of Reproductive Medicine.* 1998; 43(5): 429–434.

Hilton, P. A clinical and urodynamic study comparing the Stamey bladder neck suspension and suburethral sling procedures in the treatment of genuine stress incontinence. *Br J Obstet Gynecol.* 1989; 96: 213–220.

Hilton, P. and Stanton, S.L. A clinical and urodynamic assessment of the Burch colposuspension for genuine stress incontinence. *Br J Obstet Gynecol.* 1983; 90: 934–939.

Ulmsten, U. and Petros, P. Intravaginal slingplasty (IVS): An ambulatory surgical procedure for treatment of female urinary incontinence. *Scan J Urol Nephrol.* 1995; 29: 75–82.

Hilton, P. The role of urodynamics in pelvic floor re–education. *Pelvic Floor Re–education: Principles and Practice.* London. Springer–Verlag. 1994; 51–63.

McGuire, E.J. and Lytton, B. Pubovaginal sling procedure for stress incontinence. *J Urol.* 1978; 119: 82–84.

Blaivas, J.G. and Jacobs, B.Z. Pubovaginal fascial sling for the treatment of complicated stress urinary incontinence. *J Urol.* 1991; 145: 1214–1218.

Muller, S.C., Steinbach, F., Maurer, F.M., Melchior, S.W., Stein, R. and Hohenfellner, R. Long–term results of fascial sling procedure. *Int Urogyn J.* 1993; 4: 199–203.

Henriksson, L. and Ulmsten, U. A urodynamic evaluation of the effects of abdominal urethrocystopexy and vaginal sling urethroplasty in women with stress incontinence. *Am J Obstet Gynecol.* 1978; 131: 77–82.

* cited by examiner

METHOD FOR SURGICAL TREATMENT OF URINARY INCONTINENCE AND DEVICE FOR CARRYING OUT SAID METHOD

FIELD OF THE INVENTION

The present invention relates firstly to a surgical device and secondly to a method for surgically treating urinary stress incontinence in women.

More particularly, the present invention relates to a device for percutaneous treatment of urinary stress incontinence in women using a synthetic sub-urethral tape.

BACKGROUND OF THE INVENTION

For a long time, urinary stress incontinence has been treated under local, regional or general anesthetic, by supporting the urethra or bladder neck, in particular by using a tape.

U.S. Pat. No. 5,899,909 describes a method and a device for treating incontinence. The device enables a tape surrounded by a sheath to be implanted beneath the urethral canal, the sleeve then being withdrawn after implanting the tape. That device comprises two large needles located at either end of the tape-sleeve assembly, the needles comprising means on their proximal ends for mounting on a handle or a manipulator during the surgical intervention. Further, the tape-sleeve assembly is fixed to the proximal end using a plastic ring.

The tape is implanted by introducing each of the two needles in succession either side of the urethra, via an incision made in the anterior vaginal wall. Using each of the needles and holding them by the handle or introducing means fixed at its proximal end, the surgeon manipulates each needle to loop round the bladder and the pubic bone and exit via the abdominal wall in the suprapubic region.

The plastic sleeve surrounding the tape is presented cut at its centre and thus comprises two sections, the two sections overlapping, and the sleeve is thus removed by pulling on the ends of each of the sections which exit via each of the suprapubic cutaneous incisions.

That device and those known methods suffer from a number of disadvantages.

The device requires the use of an introducing means which has been specially designed for that type of surgical intervention. Further, the surgical intervention itself suffers from a major disadvantage in that the bottom-to-top track of the two large needles introduced into the anterior vaginal wall and exiting in the suprapubic region is not easy to control precisely, in particular when going around the base of the bladder, and vesical perforations are far from uncommon. This is upheld by medical publications. Thus it is recommended that a cystoscopy be performed during the intervention after passage of each needle. The use of that device also necessitates the use of a further accessory element, namely a rigid probe guide.

Those two accessories (introducing means and rigid guide) must thus be available to the surgical team for each intervention and has to be prepared by washing, packaging and serialization for each use.

Further, there is also a risk of vascular lesions which cannot be hidden: lateral passage with respect to the bladder with a vaginal point of entry runs the risk of injuring the epigastric and iliac vessels in the retrocrural region, with the points of the needles. Such lesions have already been recorded.

Finally for that method, if the cystoscopy confirms that the track of the tape-sleeve assembly is incorrect, it is very difficult to form a repeat track with the same device under suitable conditions. Reversing is difficult and exacting, not only for the tape-sleeve assembly, but also for the large needles. During these repetitive movements, the tape can often be uncovered due to the non hermetic nature of the sleeve. If the track is unsuitable, the sleeve-tape assembly has to be sectioned, for example at the needles, and the device can no longer be used properly for producing a further track.

Thus no percutaneous treatment exists for female urinary stress incontinence which uses a tape which can lead to the devices and technique of the present invention.

SUMMARY OF THE INVENTION

The present invention provides a method for treating urinary incontinence in a woman suffering from urinary stress incontinence, said method comprising at least the following steps:

a) forming an opening in the anterior vaginal wall;

b) creating, from two small suprapubic incisions formed in the abdominal skin, a right track and a left track from the abdominal skin to the opening formed in the anterior vaginal wall;

c) using a needle and an intermediate traction element to follow one of the tracks; and following the other with the needle and optionally an intermediate traction element;

d) verifying by cystoscopy that the path of these tracks is outside the bladder and the urethra;

e) using a support tape surrounded by a plastic sleeve to follow the tracks by passage under half of the inferior surface of the urethra;

f) adjusting the loop formed by the sleeved tape under the inferior surface of the urethra;

g) removing the sleeve by pulling towards the outside via the small abdominal incisions;

h) leaving the freed tape implanted from the first to the second incision, going round the urethra and serving to support the urethra.

It also provides a device for treating feminine urinary incontinence essentially constituted by:

a) a penetrating needle having a partially curved distal portion termed the active portion, which is integral with a straight portion having a proximal end;

b) a hermetically sleeved support tape having a distal end and a proximal end;

c) at least one intermediate traction element disposed between the penetrating needle and the sleeved tape, and having a proximal end and a distal end.

Thus the present invention overcomes the disadvantages of the known devices and methods by proposing a different operating technique and an original device which is suitable for implementing this method.

The operating technique of the invention is easier, faster and safer in particular as regards the vessels. The risk of vascular lesion does not exist because of the orientation and the given direction of the needle right from the start. The risk of vesical puncture is small even in the case of previous interventions in this regard, as is particularly frequent in this type of pathology. Using the device and operating method of the invention, the percutaneous route is used to form top-to-bottom tracks using the needle, i.e., penetrating via abdominal cutaneous mini-incisions to exit via a previously formed vaginal opening. Detachment of the vagina allows the index finger of the surgeon to be insinuated up to the lower rim of the pubis and thus enables the track of the needle to be precisely directed.

The device of the invention enables this track to be made from top to bottom on both sides and enables the absence of vesical puncturing to be confirmed by cystoscopy before engaging the sleeve-tape system.

Further, the device of the invention is capable of being re-used very readily in the event of introduction into the body along a track which proves not to be optimal, for either of the tracks. The risk of septic contamination of the sleeved tape generated by repeating manoeuvres can be removed. It should be noted that the need to re-form one of these tracks is a very rare event when using the present method, which only occurs. in the case of very strong adhesions of the bladder to the posterior surface of the pubis due, for example, to previous surgical interventions.

BRIEF DESCRIPTION OF THE DRAWINGS

Further characteristics and advantages will become apparent from the following detailed description made with reference to the accompanying drawings in which.

DETAILED DESCRIPTION

Figure 1:
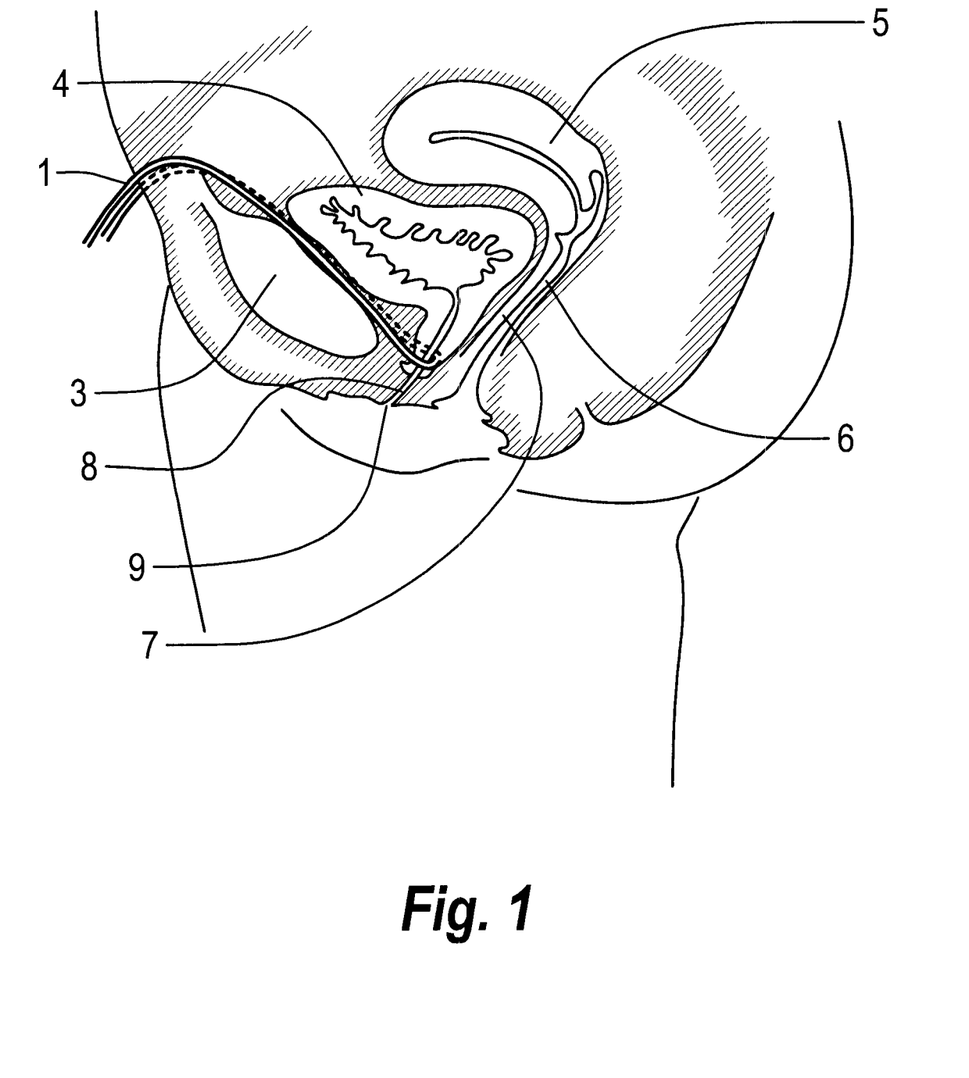
FIG. 1 shows, in profile, the location of the tape in position with respect to the abdominal wall, pubis, bladder, urethra and vagina.

In FIG. 1, tape 1 is shown in position in the patient's body, its ends not yet having been cut off at the surface of the abdominal cutaneous wall 2. Tape 1 is positioned along the posterior wall of the pubis 3 and forms a loop around the urethra 8 terminated by the urethral meatus 9. An incision or opening has been made in the anterior wall 7 of the vagina 6, beneath the uterus 5.

Device

1) The penetrating needle is produced from stainless steel. It is constituted by two integral portions screw connected to each other. The active distal portion 13 of needle 12 is partially curved and has a round cross-section; its proximal end 15 is terminated by a male screw connecting piece. Each end of the proximal 16 and distal 17 ends of the straight portion 14 of the needle has a female screw connecting piece. The length of this straight portion is 20 to 25 cm. The diameter of the needle assembly does not exceed 25 mm.

The proximal portion 16 of the needle is flattened and ribbed. This enables the surgeon to grip it and allows the needle to be oriented correctly.

2) The intermediate traction element is constituted by a hollow PVC tube with a diameter which is identical to that of the needle. It is 40 to 50 cm long. Its distal end 19 and proximal end 20 comprise a male screw connecting piece. This screw connecting piece is integrally fixed to the traction element by adhesion and screwing. The intermediate traction element is blue in colour so that it can readily be located during cystoscopy in the event of a vesical puncture.

3) The tape-sleeve system. The support tape is hermetically surrounded by a plastic sleeve. The tape is constituted by a knitted macroporous material, for example a wide mesh monofilament polypropylene. The tape is between 10 and 14 mm wide; it is 30 to 50 cm long, preferably about 40 cm.

Tape 21 can have a re-absorbable hydrophilic film in its central portion which reduces the risk of erosion or sclerosis of the urethra to a minimum. This central zone is indicated by a coloured marker.

In a variation, the tape can be constituted by other biologically acceptable materials.

A plastic sleeve completely surrounds the tape in a sealed manner. It is constituted by a strong low friction material such as a fluoropolymer. Its proximal end is closed. The other is heat-shrunk over a female screw connecting piece. The centre of the sleeve has a means for cutting and separating such as a cutting filament located perpendicular to the longitudinal axis of the sleeve, or any other means which enables the sleeve to be separated at the end of the procedure into two halves which will slide eccentrically to completely free the tape.

Operating Procedure

Figure 2A:
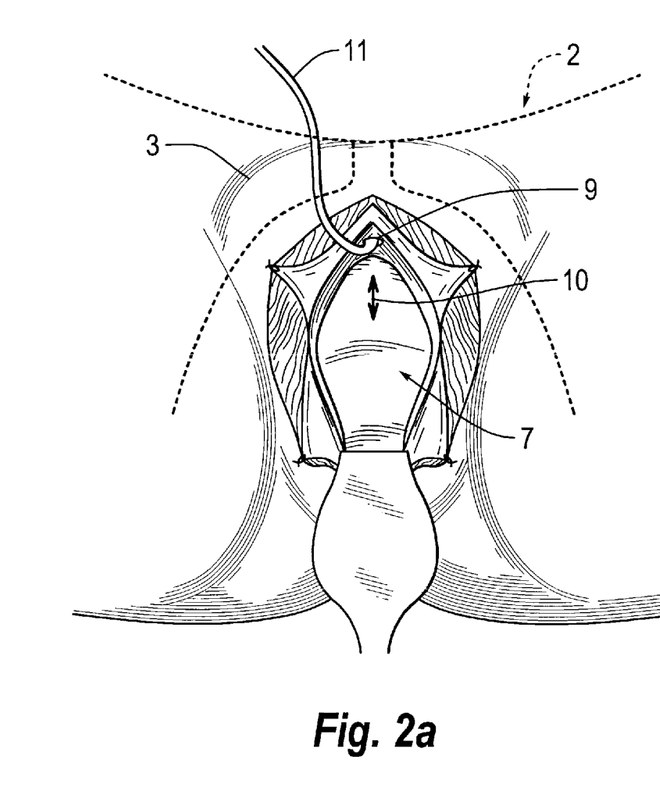
FIGS. 2a to 2h are diagrams of certain steps in the operating procedure.
Figure 2B:
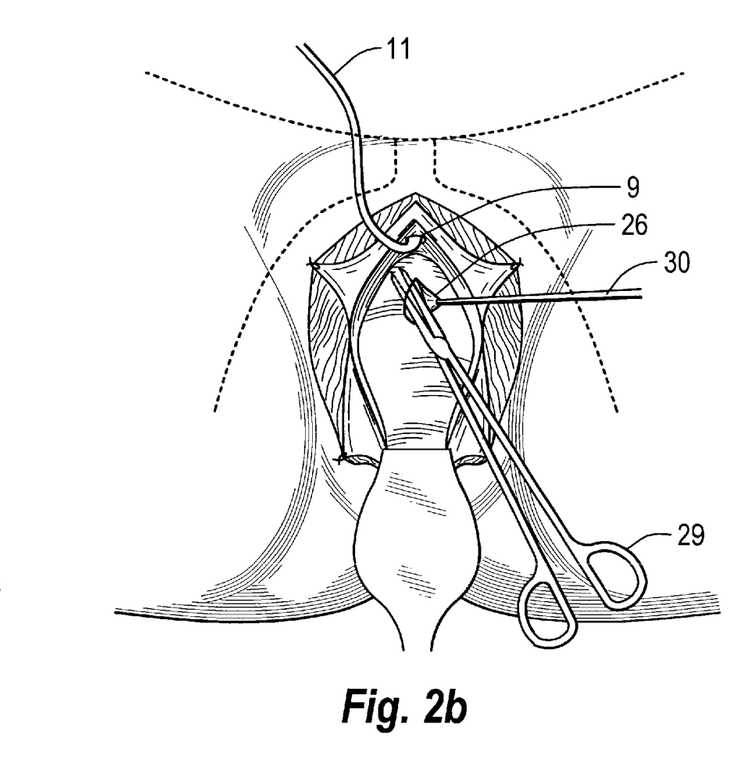

The first stage is illustrated in FIG. 2a: the patient is placed in the gynaecological position. A sterile operating area is made. A urethral balloon probe 11 is positioned in the bladder and connected to a sterile collecting bag to empty and collapse the bladder. A short vertical incision 10, maximum 30 mm in length, is made in the middle of the vaginal wall 7 centred in the middle third of the urethral canal 9. Each lip 26 of the vaginal incision 10 is detached from its subjacent tissues using scissors as shown in FIG. 2b.

Figure 2C:
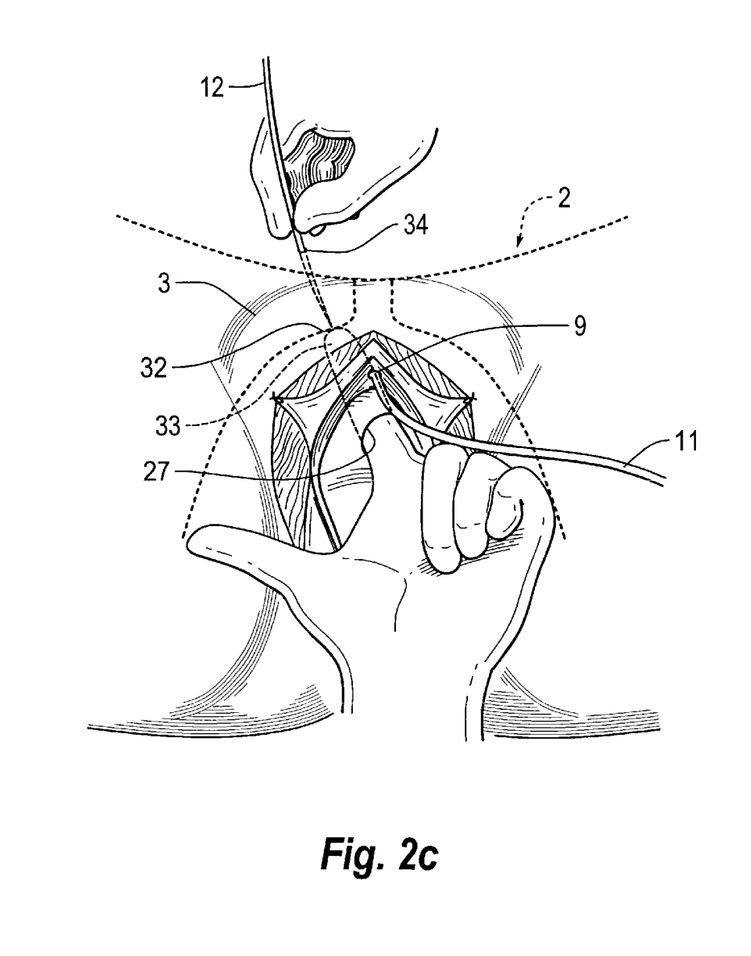

Detachment is carried out until the index finger 33 of the surgeon, introduced via the opening 27, can reach the lower rim 32 of the pubis outside the urethra and the periurethral tissues (FIG. 2c).

Then a very small cutaneous incision 34 less than 10 mm in length is made in the abdominal skin 2 immediately above the pubis 3 either side of the medial line and about 20 mm beyond it, to allow percutaneous passage of needle 12 by skimming the posterior surface of pubis 3 in the direction of the vagina.

Index finger 33 of the surgeon is insinuated into the vaginal track already prepared by detachment and the active distal end of needle 12 will come into direct contact with this index finger 33. The needle can then exit via the vaginal opening 27 and the bladder is completely safe.

Figure 2D:
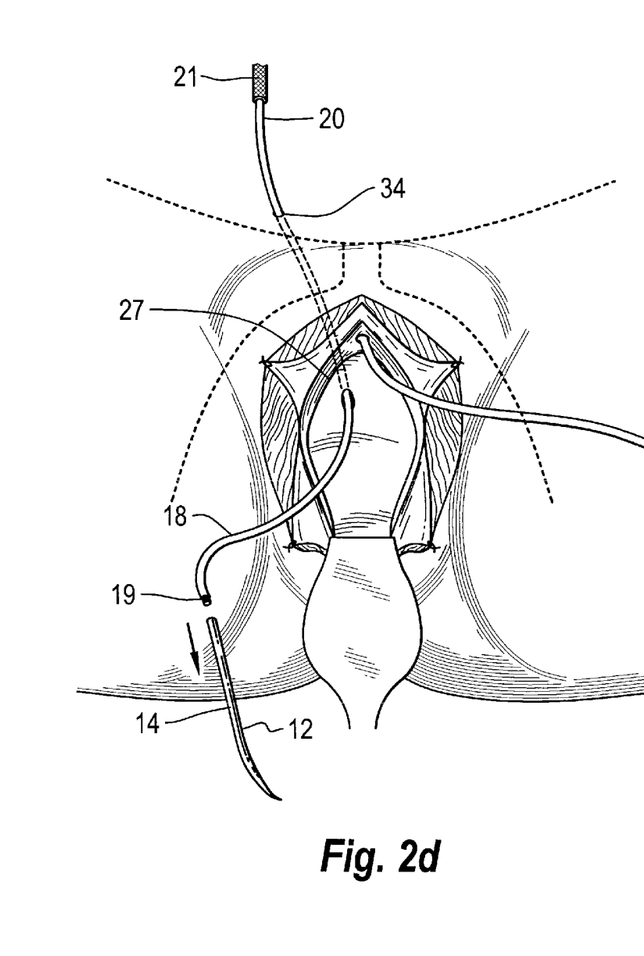

In general, the right percutaneous track is made first. Distal end 19 of the intermediate traction element 18 exits after needle 12 from the vaginal opening. This distal end 19 of the traction element is unscrewed from the proximal end 16 of the needle (arrow in FIG. 2d).

The needle is then passed into the second side (left) (FIG. 2e) in the same manner as for the first side (right). Once the curved distal portion 13 of needle 12 is well outside the vaginal opening 27, it can be detached by unscrewing (single arrow in FIG. 2e) its proximal straight portion.

Figure 2E:
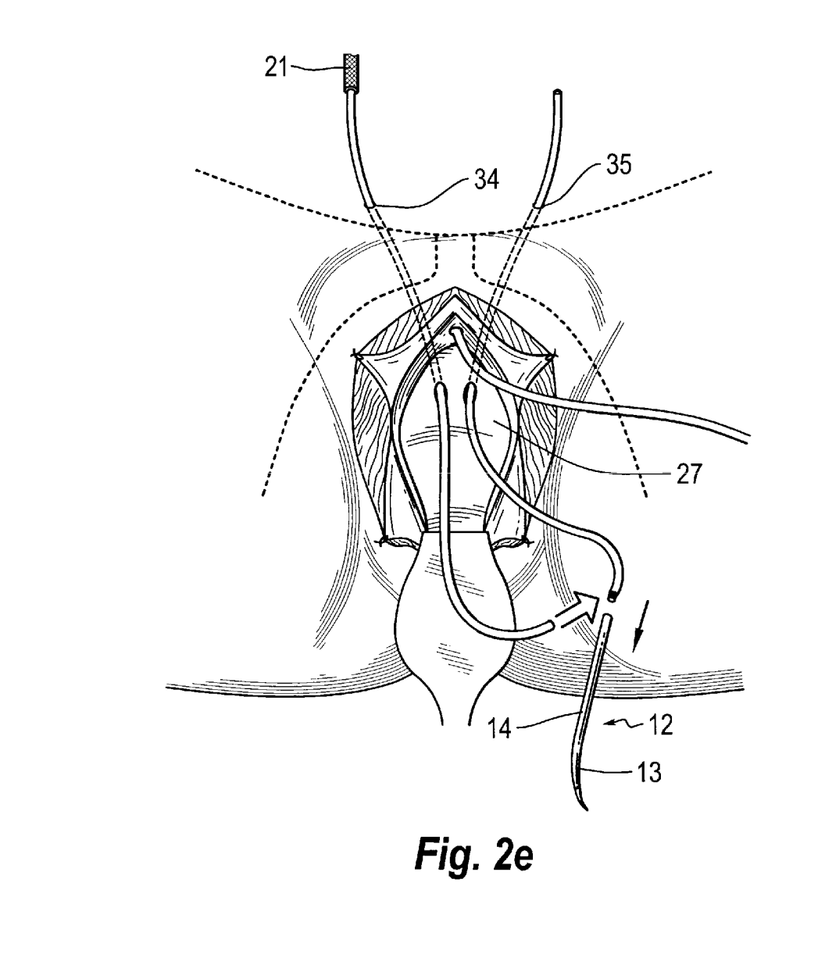

The next stage consists of screwing to connect the distal end 19 of the intermediate traction element to the straight portion 14 of the needle (double arrow in FIG. 2e).

Figure 2F:
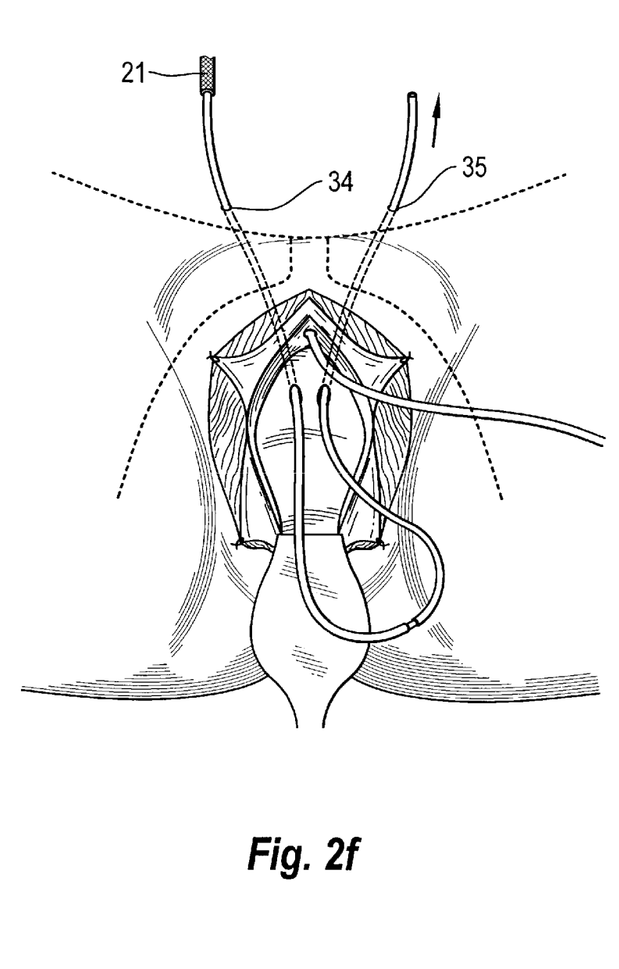

This straight portion 14 of needle 12 is then pulled out from the abdomen and as a result, a portion of the traction element to which it is attached is pulled along the second track in the direction of the arrow which is shown in FIG. 2f.

Figure 2G:
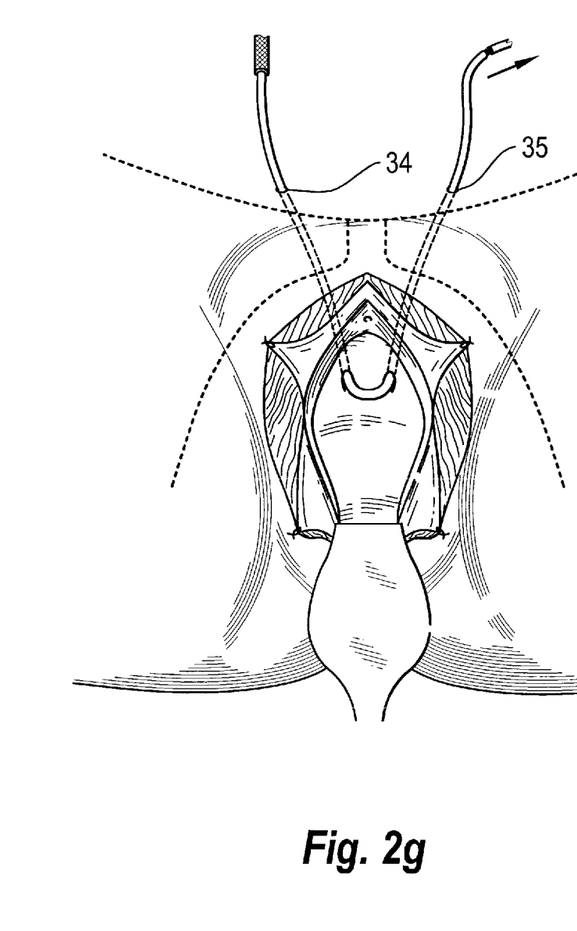
Figure 2H:
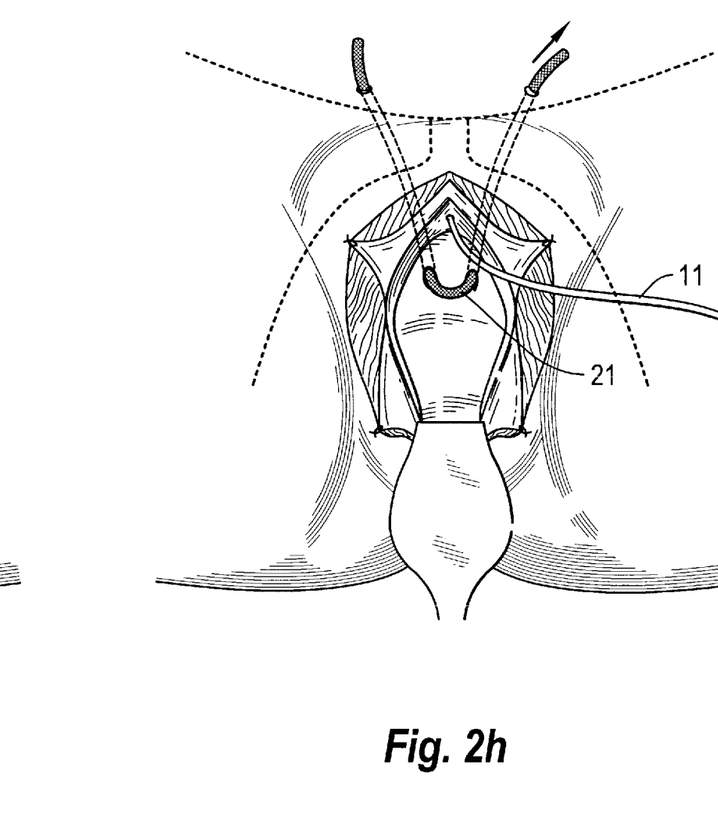

The intermediate traction element thus forms a loop around the urethra and the two ends exit respectively via abdominal incisions 34, 35 (FIG. 2g).

Urethral probe 11 is then withdrawn and cystoscopy is used to verify the absence of puncturing by this traction element.

Once verified, the end with the female connecting piece of the sleeve-tape assembly 21 is screwed to the male connecting piece of the proximal end 20 of the intermediate traction element and the assembly is pulled to position the tape surrounded by its sleeve which forms a loop around the urethra, in the place of the traction element, and the two ends exit via the abdominal cutaneous orifices 34, 35.

The two ends of the sleeve and tape are sectioned and the sleeve is separated into two halves at its middle at opening 27; the two halves are completely removed via incisions 34, 35, finally freeing the support tape.

The denuded tape is then adjusted to be placed below the inferior face of the urethra, usually in its central portion, without traction and without crushing.

If cystoscopy establishes that the track of the loop formed by the intermediate traction element is unsuitable, and more specifically confirms a vesical puncture, the side of the loop where the track is unsuitable is withdrawn and a new track is formed with the needle, as before, to produce a suitable track on this side.

The device allows top-to-bottom passage of the needle on both sides and the risk of lesions to vessels is removed and the risks of vesical lesion is much reduced.

The top-to-bottom constitution of both sides is only possible because of the highly original nature of the penetrating needle which comprises two portions which can be screwed one onto the other.

The concept of an intermediate traction element in the device of the invention is particularly innovative and advantageous; it renders the needle and the sleeved tape both integral and independent. It allows prior formation of the whole of the looped track and verification of the proper positioning of the track before handling the tape-sleeve system. This advantage is rendered possible by the suitable length of the traction element.

If it proves necessary, it enables a new track to be formed for the right side and for the left side before any manipulation of the sleeved tape.

Terminal manipulation of the sleeved tape reduces the risk of septic contamination, the surgeon changing gloves and cleaning the operating area again if necessary before this terminal phase.

Figure 2I:
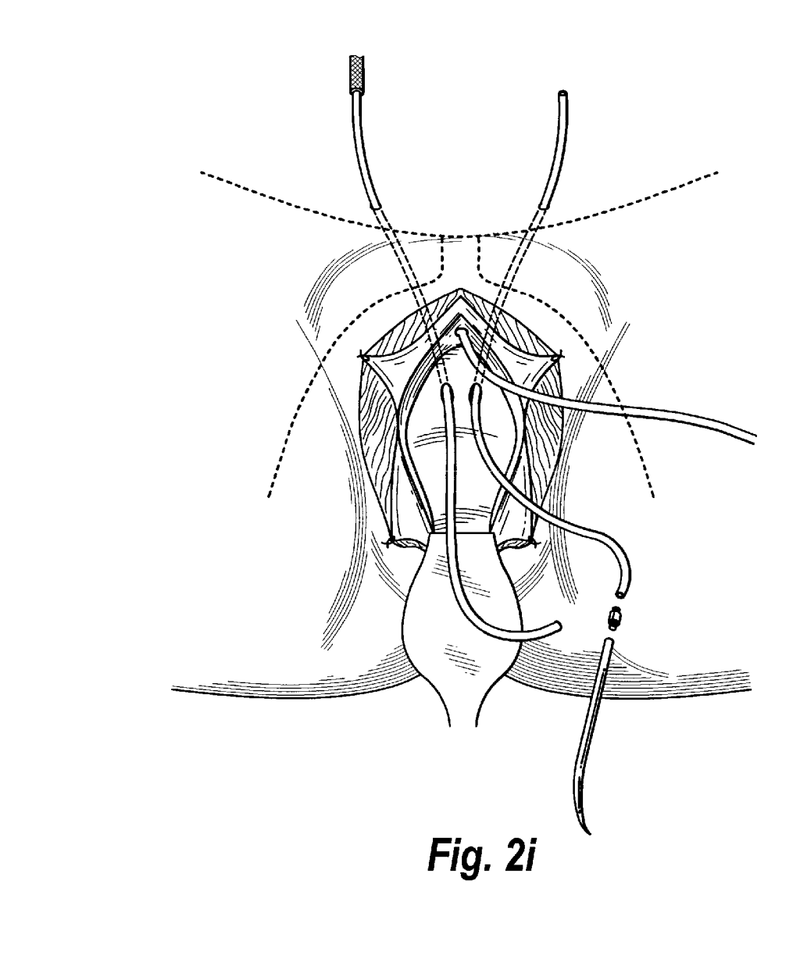
FIGS. 2i and 2j are diagrams of alternatives to certain of steps 2a to 2h.

The intermediate traction element can have other embodiments:

The tube can be formed from any suitable material with mechanical characteristics which are similar to that of PVC. This tube, in PVC or the like, can also be separated into two portions of similar length, for example equal lengths, by cutting it at its centre. A short intermediate piece, for example of metal, with a diameter similar to that of the tube and having a male screw portion 24, 25, can then be envisaged; such a part 23 is shown in FIG. 2*i*, the male screw element corresponding to the internal diameter of the tube. Any other means which can directly and integrally connect the two tubular halves can also be envisaged, once the right and left tracks formed using the needle passed from top to bottom to the right and the left in succession are joined.

When using a tube, parts similar to part 23 can be used to removably fix the traction element to the needle and to the tape and the portions of the traction elements to each other. Parts carrying a male and a female connecting piece can also be envisaged, for ease of fixing. Other fixing systems other than screw systems can be provided for the removable or non removable fixings.

Figure 2J:
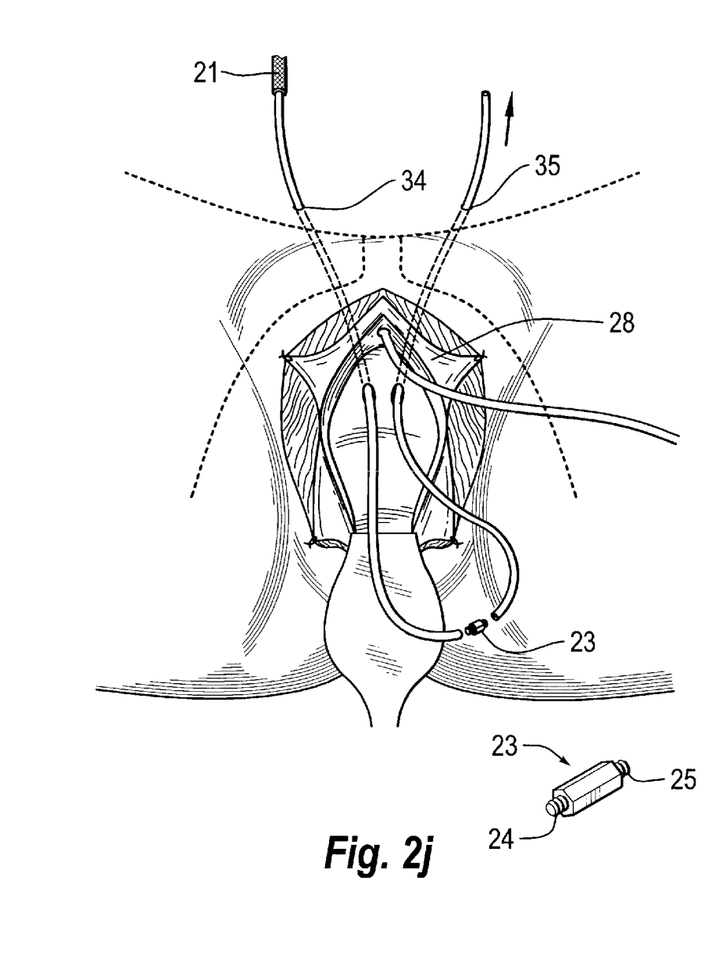

In this variation, a one-piece needle is used which can terminate in a male screw connecting piece. Passage of the track on each right and left side is made by screwing a portion of the traction element (FIG. 2I) to the proximal end of the needle. Cystoscopy then verifies the absence of punctures; then the two tubular halves are connected to each other using the small metal part to form a single traction element disposed in a loop beneath the urethra (FIG. 2*j*). The remainder of the intervention is identical.

In a variation, a fluoropolymer lace can constitute the traction element. In this case, it is connected to the needle via an eye at its proximal end and is folded back on itself after passage through the eye and sewn to itself. In this variation of the device, the lace, which is about 40 cm long, can be sectioned at its centre when carrying out the operation employing the fundamental general principle of forming a top-to-bottom track; and again it can be reconstituted by the surgeon by a simple mattress suture.

The sleeve material, which may be formed from Teflon or based on a fluoropolymer, provides the internal and external surfaces of the sleeve, firstly to endure good separation between said sleeve with advantageous non-stick properties and the tape and secondly to limit friction and avoid trauma during passage inside the patient's body.

A non-stick film opposite the lower surface of the urethra can be provided to protect the patient from the risk of erosion or sclerosis around the urethra.

The needle is unique and, for its penetration, does not need any additional instrument to grip it, which saves time in preparation for surgery and during surgery.

The ease of use and simplicity of the constituent elements of the device also have cost advantages.

The ensemble of the elements of the device of the invention can be re-used in the event of poor manipulation and if the track inside the patient's body is to be improved or optimised. This represents a considerable advantage over the prior art technique.

Since the tracks can be produced from top to bottom, the device improves safety for the patient and the quality of the therapeutic result.

The effect of the tape on continence and regulation have not been evaluated in the method of the invention for at least the following two reasons:
- continence in the prone position is not comparable to that when upright; and
- the efficacy of the tape is not only explained by a tightening effect (which risks causing dysuria) but also by a supporting effect on the inferior surface of the urethra and by a lateral bracing effect. In the prior art, continence was monitored after filling the bladder and coughing to adjust the tension of the tape.

Finally, using the device and operating procedure of the invention, the surgeon can choose the height of the position of the tape with respect to the urethral channel (proximal or central portion) for each patient based on clinical, urodynamic and possibly imaging and endoscopy data, a feat which cannot be achieved using a prior art technique.

What is claimed is:

1. A method for treating urinary incontinence in a woman suffering from urinary stress incontinence, said method comprising at least the following steps:
   a) forming an opening in the anterior vaginal wall;
   b) forming two small suprapubic incisions in the abdominal wall, and creating a right track and a left track extending from the abdominal skin to the opening formed in the anterior vaginal wall, by penetrating from the abdominal skin to exit via the opening formed in the anterior vaginal wall;

c) using a needle and an intermediate traction element to follow one of the tracks from one of said small suprapubic incisions to the opening formed in the anterior vaginal wall, and following the other track with the needle and optionally an intermediate traction element;

d) verifying by cystoscopy that the path of these tracks is outside the bladder and the urethra;

e) using a support tape surrounded by a plastic sleeve to follow the tracks by passage under half of the inferior surface of the urethra;

f) adjusting the loop formed by the sleeved tape under the inferior surface of the urethra;

g) removing the sleeve by pulling towards the outside via the small abdominal incisions;

h) leaving the support tape implanted from the first to the second incision, going round the urethra and serving to support the urethra.

2. The method of claim 1, in which each track is produced using a needle inserted via the lower suprapubic incision and guided along the posterior surface of the pubis in contact with the finger of the surgeon introduced via the opening to the lower rim of the pubis on the same side.

3. The method of claim 1, in which the distal end of the tape is connected to the proximal end of the traction element after said verification.

4. The method of claim 1, in which the sleeve is cut in the central region.

5. The method of claim 1, in which the incision in the vaginal wall is T or I shaped.

6. The method of claim 1, in which vaginal detachment is carried out.

7. The method of claim 1, in which a urethral probe is first inserted.

8. A device for treating feminine urinary incontinence essentially constituted by:

a) a penetrating needle having a curved portion with an active distal end, which is integral with a straight portion having a proximal end;

b) a hermetically sleeved support tape having a distal end and a proximal end, the distal end being connected to the proximal end of the needle;

c) at least one intermediate traction element having a distal end connected to the proximal end of the needle and a proximal end which can be fixed to the distal end of the sleeved tape.

9. The device of claim 8, in which the cross section of the distal end of the needle is round and the cross section of the proximal end of the needle is substantially rectangular.

10. The device of claim 8, in which the sleeve of the tape is divisible at its centre.

11. The device of claim 10, in which the diameter of the distal end of the needle is about 0.5 mm and the cross section of the proximal end is about 2 mm×3 mm, the length of the proximal straight portion being about 20 cm.

12. The device of claim 8, in which the at least one traction element is at least one tube or lace.

13. The device of claim 12, in which the sleeve and/or at least one lace is (are) formed from a fluoropolymeric type material.

14. The device of claim 12, in which the tube is formed from PVC and its diameter is about 2.5 mm.

15. The device of claim 8, in which the tape is formed from a macroporous knitted material.

16. The device of claim 8, in which the tape comprises a hydrophilic non-stick film at its central portion.

17. The device of claim 8, in which the sleeve is formed from heat shrinkable material.

18. The device of claim 8, in which the straight portion of the penetrating needle has a ribbed surface over at least a portion thereof.

19. The device of claim 8, in which the needle and the traction element are screwed together to render them integral.

20. The device of claim 8, in which the traction element is constituted by two portions which are of substantially the same length, removably joined together.

21. The device of claim 8, in which a double male screw portion connects the two portions of the tubular traction element or one of its portions to the needle or to the tape.

22. The device of claim 21, in which the curved portion and the straight portion of the needle are screwed together to render them integral and removable.

* * * * *